United States Patent [19]

Selvidge

[11] Patent Number: 4,522,595
[45] Date of Patent: Jun. 11, 1985

[54] DENTAL TOOL FOR CLEANING TEETH INTERPROXIMALLY

[76] Inventor: Leroy Selvidge, 1108 Mimosa Dr., Oxford, Miss.

[21] Appl. No.: 498,702

[22] Filed: May 27, 1983

[51] Int. Cl.³ .............................................. A61C 3/00
[52] U.S. Cl. .................................... 433/142; 132/93
[58] Field of Search ............... 132/84 A, 89, 90, 93; 433/142; 15/110

[56] References Cited

U.S. PATENT DOCUMENTS

| | | |
|---|---|---|
| 58,631 | 10/1866 | Gates . |
| D. 121,506 | 3/1935 | Davis . |
| D. 242,883 | 1/1977 | De Marco . |
| 982,232 | 1/1911 | Bartholomew . |
| 1,086,936 | 2/1914 | Pounder et al. . |
| 2,016,597 | 10/1935 | Drake ................... 433/142 |
| 2,091,511 | 8/1937 | London .............. 128/62 A |
| 2,614,556 | 10/1952 | Staunt ................. 128/62 A |
| 3,987,549 | 10/1976 | Robertelli . |
| 4,185,388 | 1/1980 | Jarby . |

FOREIGN PATENT DOCUMENTS 2748343  3/1959  Fed. Rep. of Germany ... 128/62 A

OTHER PUBLICATIONS

Roto-Pro Advertisement by Ellman Int'l Mfg. Co., Hewlett, New York.
PY-CO-PAY Advertisement by Dental Products Div., Block Drug Co., Jersey City, N.J.
STIM-U-DENT Advertisement by Johnson & Johnson, New Brunswick, N.J.
Prior Invention of Applicant submitted to John O. Butler Co., Chicago, Ill., dated Feb. 4, 1981.

*Primary Examiner*—Robert Peshock
*Attorney, Agent, or Firm*—Larson and Taylor

[57] ABSTRACT

A dental tool for the cleaning of teeth interproximally is disclosed. The dental tool includes an elongate shank with a resilient tip located around one end of the shank. The tip is designed to be deformably insertable interproximally and has a pear-shaped cross section. Preferably, the shank is attached to a handle which is conveniently the end of a toothbrush. The tip and shank can be integrally formed of a rubber material, or the shank can be made of metal and the tip of a rubber material. Ribs are also provided around the periphery of the tip.

9 Claims, 5 Drawing Figures

DENTAL TOOL FOR CLEANING TEETH INTERPROXIMALLY

FIELD OF THE INVENTION

The present invention relates generally to devices for cleaning teeth, and more particularly to a device for the cleaning of teeth interproximally.

BACKGROUND OF THE INVENTION

The at home cleaning of teeth and massaging of gums have long been recommended by dentists. As the importance of cleaning hard-to-reach places has been realized, various devices have been proposed for cleaning or massaging these areas. Perhaps the most widely used method is flossing. While this method of cleaning and massaging is highly effective, certain interproximal areas of teeth are concave shaped and cannot be reached with floss.

A number of prior art devices which are used for massaging the gums also effect some incidental cleaning of the interproximal areas. For example, the product STIM-U-DENT produced by Johnson and Johnson is recommended for patients who can not or will not floss. This product is made of soft, porous basswood and has a tapered, flat-bottomed wedge shape. Various other rubber wedge-shaped tips for massaging gums have also been disclosed such as the PY-CO-PAY toothbrush produced by Block Drug Company, Inc. of Jersey City, N.J. and that disclosed in U.S. Pat. No. 1,086,936 (Pounder et al). A wedged-shaped toothbrush is also disclosed in U.S. Pat. No. Des. 242,883 (De Marco). Due to the wedge-shape of these devices, the incidental interproximal cleaning of teeth is limited and any attempt to effect more cleaning results in the wedge being caught between the teeth.

A number of devices comprising a steel shank with a rubber tip have been disclosed in the prior art for use with a dental handpiece. The dental handpiece causes the tip to rotate and generally the tip is used for polishing amalgam restorations (silver fillings). Typical of these so called "polishing points" is that disclosed in U.S. Pat. No. 4,185,388 (Jarby) and in U.S. Pat. No. 3,987,549 (Robertelli).

It has also been disclosed in the prior art to provide a steel burr in a dental handpiece where the rotation of the steel burr is used to clean calculus from the teeth. Various shapes have been proposed for these steel burrs including wedged shaped burrs and round tip burrs provided by Ellman International Manufacturing, Inc. of Hewlett, N.Y. A ribbed oblong shaped tip for use in drilling a tooth has also been disclosed in U.S. Pat. No. 58,631 (Gates).

The at home massaging of gums with a device similar to a prophy cup has also been disclosed in U.S. Pat. No. Des. 121,506 (Davis). The toothbrush design shown in this patent includes a single prophy cup shaped member at one end of the toothbrush.

Although much attention has been directed to the massaging of gingivae and cleaning of teeth, the effective cleaning of interproximal areas of posterior teeth has not been achieved by prior art devices.

SUMMARY OF THE INVENTION

In accordance with the present invention, a dental tool for cleaning teeth interproximally is provided. The dental tool includes an elongate shank having a longitudinal axis and a resilient tip located around one end of the shank. The resilient tip is designed to be deformably insertable interproximally, and the tip is provided with a pear-shaped cross section when viewed in a plane containing the axis of the shank. Preferably, a handle is provided to which the shank is attached. In use, the resilient tip is inserted in the interproximal space and presses against the areas of the tooth, particularly the concave areas, to effectively clean these areas.

In a preferred embodiment of the present invention, the handle is one end of a toothbrush handle and the shank is mounted perpendicular to the longitudinal axis of the handle. In one embodiment of the present invention, the tip and the shank are intergally formed of a rubber material. In another embodiment, the shank is made of suitable metal such as steel while the tip is made of a rubber material which is attached to the shank. If desired, the tip can be provided with ribs around the periphery thereof.

It is an object of the present invention to provide a dental tool for cleaning of teeth interproximally which is usable at home by those with no specialized skill.

It is a feature of the present invention that the dental tool provided for the cleaning of teeth interproximally is easy and simple to use and will not harm the teeth of the user even if used improperly.

Other features and advantages of the present invention are stated in or apparent from a detailed description of presently preferred emboidments of the invention found herein below.

DETAILED DESCRIPTION OF THE PREFERRED EMBODIMENTS

Figure 1:
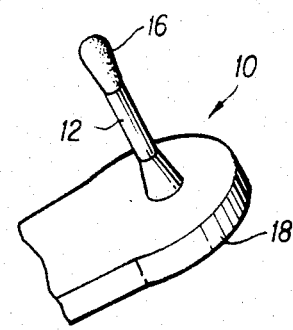
FIG. 1 is a perspective view of the dental tool according to the present invention attached to a handle.
Figure 2:
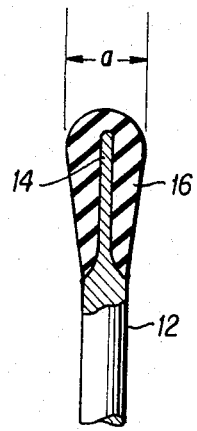
FIG. 2 is a cross-sectional elevation view of the dental tool depicted in FIG. 1.

With reference now to the drawings in which like numerals represent like elements throughout the several views, a presently preferred embodiment of a dental tool 10 is depicted in FIGS. 1 and 2. Dental tool 10 includes an elongate shank 12 having a reduced end 14. Attached to reduced end 14 is a tip 16. Conveniently, shank 12 is made of a rigid material, such as steel or other suitable metal, and tip 16 is made of a suitable resilient material such as rubber. As shown in greater detail in FIG. 2, tip 16 has a pear shape when viewed in cross section. Conveniently, the other end of shank 12 is securely attached to a handle 18, such as the end of a toothbrush handle opposite the brush portion. For ease of use, shank 12 is perpendicular to the longitudinal axis of handle 18.

As tip 16 is designed to be inserted into the interproximal areas between two teeth, the diameter "a" of tip 16 is designed to be deformably insertable therein. Diameter "a" is between 0.5 and 2.0 mm. and preferably about 1.0 mm. In order to securely attach tip 16 to shank 12, and to allow tip 16 to resiliently deform, the diameter of reduced end 14 should be between 0.075 and 0.2 mm.

and preferably about 0.1 mm. To allow for intraoral use of dental tool 10, shank 12 should be between 5.0 and 15.0 mm. in length.

Figure 3:
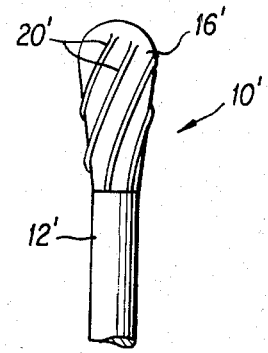
FIG. 3 is an elevational view of an alternative embodiment of a dental tool according to the present invention.

Depicted in FIG. 3 is an alternative embodiment of a dental tool 10' having a shank 12' and tip 16. In this embodiment, the outer surface of tip 16' is provided with a plurality of small raised portions or ribs 20'. Preferably, ribs 20' are integrally formed with tip 16'.

Figure 4:
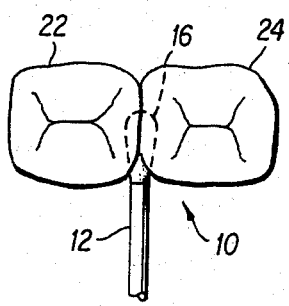
FIG. 4 is a plan view depicting the insertion of the dental tool interproximally.
Figure 5:
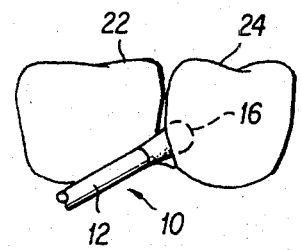
FIG. 5 is an elevational view depicting the insertion of the dental tool interproximally.

Dental tool 10 is used in the following manner as depicted in FIGS. 4 and 5. Initially, the user grasps handle 18 and positions tip 16 opposite the interproximal space between two teeth 22 and 24. Handle 12 is then used to force tip 16 into the interproximal space where tip 16 resiliently deforms against the interproximal areas of teeth 22 and 24. It should be noted that the resiliency of tip 16 causes the surface thereof to be pressed into any concavities along the interproximal surfaces of teeth 22 and 24. As tip 16 is rubbed along the interproximal surfaces of teeth 22 and 24, the surfaces are cleaned of plaque and polished. This polishing effect can be used to remove scratches which have been formed in these areas during calculus removal using a metal burr or the like in a dental handpiece. It should be appreciated that the pear shape of tip 16 facilitates the ability of tip 16 to be deformably inserted in the interproximal areas between teeth 22 and 24, and to resiliently press against the interproximal surfaces to clean these areas of teeth 22 and 24.

Where ribs 20' are provided on tip 16' of dental tool 10', a rotation about the longitudinal axis of shank 12' effects a further cleaning and polishing of the interproximal surfaces between teeth 22 and 24. The slanted direction of ribs 20' also increase the cleaning and polishing of tip 16' as tip 16' is moved into and out of the interproximal areas between teeth 22 and 24.

It should be appreciated that the provision of a soft rubber tip 16 is noninjurious to the teeth so that the use of dental tool 10 by an unskilled user and a misuse by the user will not harm the user's teeth.

It should also be appreciated that tip 16 could be integrally formed with shank 12 of a suitable rubber material instead of the two piece construction described above.

While the present invention has been described with respect to an exemplary embodiment thereof, it will be understood by those of ordinary skill in the art that these and other variations and modifications can be effected within the scope and spirit of the invention.

I claim:

1. A dental tool for the cleaning of the subgingival interproximal concave surfaces of teeth comprising:
    an elongate cylindrical shank having a longitudinal axis and a narrow end; and
    a resilient and deformable tip located at the narrow end of said shank and larger than said shank, said tip being integrally formed and sized to be deformably insertable and rotatable interproximally, said tip also having a pear-shaped cross section when viewed in a plane containing the axis of said shank with the larger end outermost and having a maximum diameter of between 0.5 mm and 2.0 mm whereby after deformably inserting said pear-shaped tip interproximally said tip is rubbed along the concave surfaces to clean these surfaces of plaque and to polish these surfaces.

2. A dental tool as claimed in claim 1 and further including a handle to which said shank is attached.

3. A dental tool as claimed in claim 2 wherein said handle is a toothbrush handle and wherein said shank is attached to the end portion of the toothbrush opposite the brush portion and the axis of said shank is perpendicular to the longitudinal axis of said handle.

4. A dental tool as claimed in claim 2 wherein said tip and said shank are integrally formed and are made of a rubber material.

5. A dental tool as claimed in claim 2 wherein said shank is of a rigid material, and wherein said tip is made of a rubber material and is attached to said shank.

6. A dental tool as claimed in claim 5 wherein said tip has outwardly projecting ribs formed around the periphery thereof.

7. A dental tool as claimed in claim 6 wherein said ribs are slanted longitudinally to the longitudinal axis of said shank.

8. A dental tool as claimed in claim 4 wherein said tip has outwardly projecting ribs formed around the periphery thereof.

9. A dental tool as claimed in claim 8 wherein said ribs are slanted longitudinally to the longitudinal axis of said shank.

* * * * *